United States Patent [19]

Tu et al.

[11] 4,300,012

[45] Nov. 10, 1981

[54] PROCESS FOR TRANSALKYLATION OF ALKYLAROMATIC HYDROCARBONS

[75] Inventors: Hosheng Tu, Shorewood; Stephen W. Sohn, Northbrook, both of Ill.

[73] Assignee: UOP Inc., Des Plaines, Ill.

[21] Appl. No.: 206,323

[22] Filed: Nov. 12, 1980

Related U.S. Application Data

[62] Division of Ser. No. 112,762, Jan. 17, 1980, Pat. No. 4,264,473.

[51] Int. Cl.³ .......................... C07C 5/22; C07C 5/52
[52] U.S. Cl. ................................. 585/470; 585/475
[58] Field of Search ............................... 585/470, 475

[56] References Cited

U.S. PATENT DOCUMENTS

| | | | |
|---|---|---|---|
| 2,339,302 | 1/1944 | Thomas et al. | 252/432 |
| 3,374,182 | 3/1968 | Young | 252/455 Z |
| 3,954,670 | 5/1976 | Pine | 252/455 Z |
| 4,049,573 | 9/1977 | Kaeding | 252/432 |

FOREIGN PATENT DOCUMENTS 719727  10/1965  Canada ............................... 252/432

*Primary Examiner*—Curtis R. Davis
*Attorney, Agent, or Firm*—James R. Hoatson, Jr.; John G. Cutts, Jr.; William H. Page, II

[57] ABSTRACT

A catalytic composite of improved selectivity and a method of manufacture is disclosed. The catalytic composite is particularly effective with respect to the transalkylation of toluene. The catalytic composite is characterized by a method of preparation which comprises subjecting a mordenite alumina to an aqueous ammoniacal treatment at a pH of at least about 9.5; calcining the resulting mordenite to an aqueous solution containing a boron salt; and calcining the resulting mordenite alumina to provide said catalytic composite.

3 Claims, No Drawings

PROCESS FOR TRANSALKYLATION OF ALKYLAROMATIC HYDROCARBONS

This is a division of application Ser. No. 112,762 filed Jan. 17, 1980, now U.S. Pat. No. 4,264,473.

BACKGROUND OF THE INVENTION

Crystalline aluminosilicates, or zeolites, of which mordenite is one example, are well known in the art and have found extensive application as hydrocarbon conversion catalysts or as a component thereof. Such materials are of ordered crystalline structure often visualized as a three-dimensional network of fundamental structural units consisting of silicon-centered $SiO_4$ and aluminum-centered $AlO_4$ tetrahedra, the tetrahedra being interconnected by a mutual sharing of apical oxygen atoms and arranged to form cages or cavities in open communication through smaller intracrystalline channels or pore openings whose narrowest cross section has essentially a uniform diameter characteristic of each crystalline aluminosilicate variety. To effect a chemical balance, each $AlO_4$ tetrahedra has a cation associated therewith—usually a sodium or other exchangeable cation. The aforementioned cages or cavities are occupied by water molecules and by the last mentioned cations, both of which exhibit considerable freedom of movement permitting ion-exchange and reversable dehydration.

The crystalline aluminosilicates, or zeolites, employed in the manufacture of the catalytic composite of this invention, are of the mordenite crystal structure, highly siliceous in nature and generally characterized by a silica-alumina mole ratio of from about 6 to about 12 as found in nature. The mordenite crystal structure comprises four- and five-membered rings of the $SiO_4$ and $AlO_4$ tetrahedra so arranged that the crystal lattice comprises pores and channels running parallel along the crystal axis to give a tubular configuration. This structure is unique among the crystalline aluminosilicates since the channels or tubes do not intersect, and access to the cages or cavities is in only one direction. For this reason, the mordenite structure is frequently referred to as two-dimensional. This is in contrast to other well-known crystalline aluminosilicates, for example faujasite, in which the cavities can be entered from three directions. Mordenite, clinoptilolite, or mordenite which has been synthesized or acid extracted, caustic extracted or otherwise treated to increase the silica-alumina mole ratio to about 20:1 or more while maintaining the mordenite crystal structure, may be used in the manufacture of the catalytic composite of this invention.

Crystalline aluminosilicates having a mordenite crystal structure have heretofore been utilized composited with a refractory inorganic oxide, typically alumina, as a hydrocarbon conversion catalyst, and are particularly useful with respect to the transalkylation of alkylaromatic hydrocarbons.

It is an object of this invention to present a new and useful method of manufacture providing a novel catalytic composite of improved selectivity.

In one of its broad aspects, the present invention embodies a method of manufacture providing a catalytic composite of improved selectivity which comprises subjecting a mordenite alumina to an aqueous ammoniacal treatment at a pH of at least about 9.5; calcining the resulting mordenite alumina from step (a); subjecting the resulting calcined mordenite alumina to an aqueous solution containing a boron salt; and calcining the resulting mordenite alumina from step (c) to provide said catalytic composite.

Other objects and embodiments of this invention will become apparent in the following detailed specification.

DETAILED DESCRIPTION OF THE INVENTION

Pursuant to the present invention, the raw catalytic composite is prepared by admixing mordenite and alumina and forming particles which contains mordenite and alumina. These resulting particles are subjected to an aqueous ammoniacal treatment at a pH of at least about 9.5.

The aqueous ammoniacal treatment can be effected at a temperature of from about 75° to about 200° C. over a period of from about 1 to about 24 hours. The treatment can be effected at substantially atmospheric pressure in an open vessel at about the reflux temperature of the aqueous ammoniacal solution albeit over a more extended period up to about 24 hours. The treatment is effective over a substantially shorter period, say from about 1 to about 10 hours at autogenous pressures utilizing a closed vessel. Suitable ammoniacal solutions include solutions of bases such as ammonium hydroxide, hydroxylamine, hydrazine, tetramethylammonium hydroxide, etc., or strong organic amines like methylamine, dimethylamine, ethylamine, diethylamine, propylamine, diisopropylamine, n-butylamine, t-butylamine, diisobutylamine, n-amylamine, n-hexylamine, ethylene diamine, hexamethylenediamine, benzylamine, aniline, piperazine, piperadine, and the like, the selected base being employed in sufficient concentration to provide a pH of at least about 9.5, and preferably from about 10 to about 12.

The mordenite employed herein should contain or should be treated to contain, less than about 5 wt. percent sodium calculated as $Na_2O$. The sodium can be reduced to an acceptable level by conventional and widely practiced ion-exchange techniques. Typically, ammonium cations are exchanged for sodium cations on treating the mordenite in contact with an aqueous ammonium salt solution, for example, an aqueous ammonium chloride solution. The resulting ammonium-exchanged mordenite is thereafter heat-treated to effect thermal decomposition of the ammonium cations and formation of the hydrogen form of the mordenite. In any case, the treatment may be effected one or more times to reduce the sodium content to less than about 5 wt. percent calculated as $Na_2O$.

Various inorganic oxides may be used in accordance with the method of this invention, but alumina is preferred particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred.

The mordenite may be combined in intimate admixture with the alumina in any conventional or otherwise convenient manner. For example, the mordenite can be admixed with an alumina precursor subsequently converted to alumina to provide the mordenite in intimate admixture with the alumina. The mordenite may be commingled with acidic alumina sol, such as results from digesting aluminum in hydrochloric acid under controlled conditions, provided that the mordenite is not unduly exposed to the acid media, the mixture being thereafter treated at conditions effecting gelatin of the sol. For example, the mixture can be dispersed as droplets in a hot oil bath whereby gelation occurs with the formation of spheroidal gel particles substantially in accordance with the method of U.S. Pat. No. 2,620,314. In this instance, the mordenite is conveniently and advantageously commingled with an aqueous hexamethylenetetramine (HMT) solution before being admixed with the acidic sol, the HMT otherwise serving as a buffering agent in accordance with the teaching of said patent. In this manner, at least a portion of the HMT solution becomes occuluded in the mordenite to assure a less acid environment in the immediate vicinity of the zeolite during the critical period in which the acid anion content of the sol is substantially neutralized by the buffering action of the HMT to promote a progressive gelation of the sol. One preferred method comprises commingling the mordenite with a powdered alumina, adding a binder and/or lubricant to the mixture, and compressing the mixture into pills or pellets of uniform size and shape. Alternatively, and still more preferably, the mordenite is mulled with a powdered form of the alumina, and with a peptizing agent such as nitric acid, to form an extrudable dough. The dough can be pressured through a die of predetermined size to form extrudate particles utilized as such or rolled into spheres in a spinning drum prior to calcination.

In any case, the mordenite is calcined in admixture with the alumina to form a catalytic composite. Calcination is suitably in an air atmosphere at a temperature of from about 700° F. to about 1300° F. over a period of from about 0.5 to about 10 hours.

The resulting calcined mordenite alumina is subjected to an aqueous ammoniacal treatment at a pH of at least 9.5 as hereinabove described.

Another essential step in the production of the catalyst composition of the present invention is the calcination of the mordenite alumina composite subsequent to the aqueous ammoniacal treatment. The preferred conditions for calcination are those hereinabove described.

The next essential step in the production of the instant catalyst composition is subjecting the calcined mordenite alumina to an aqueous solution containing a boron salt. The boron component may be incorporated with the mordenite alumina by any suitable impregnation technique. Thus, the mordenite alumina can be soaked, dipped, suspended or otherwise immersed in an aqueous impregnation solution containing a soluble boron salt. One suitable method comprises immersing the mordenite alumina in the impregnating solution and evaporating the same to dryness in a rotary steam dryer. Another suitable method comprises dipping the mordenite alumina into the aqueous impregnating solution at room temperature until complete penetration of the mordenite alumina by the solution is achieved. After absorption of the impregnating solution, the mordenite alumina is drained of free surface liquid and dried in a calciner. In accordance with the present invention, calcination effected in an oxidizing atmosphere at a temperature of from about 700° to about 1300° F. The oxidizing atmosphere is suitably air, although other gases comprising molecular oxygen may be employed.

The catalytic composite of this invention is particularly useful for the transalkylation of alkylaromatic hydrocarbons. Thus, an alkylaromatic hydrocarbon having from about 7 to about 15 carbon atoms per molecule is treated at transalkylation conditions including a temperature of from about 200° to about 480° C. and a pressure of from about atmospheric to about 1500 pounds per square inch gauge (psig) in contact with a catalyst comprising essentially the catalytic composite of this invention to form products of higher and lower number of carbon atoms that said alkylaromatic hydrocarbon.

The alkylaromatic hydrocarbon feed stock can be a substantially pure alkylaromatic hydrocarbon of from about 7 to about 15 carbon atoms, a mixture of such alkylaromatic hydrocarbons, or a hydrocarbon fraction rich in said alkylaromatics. Suitable alkylaromatic hydrocarbons include alkylbenzenes and alkylnaphthalenes, preferably with an alkyl group of less than about 4 carbon atoms. The catalytic composite is particularly effective in the treatment of the more difficulty transalkylatable toluene to form benzene, xylenes, or other polymethylbenzenes.

The transalkylation, or disproportionation, reaction can be effected in contact with the catalytic composite of this invention in any conventional or otherwise convenient manner and may comprise a batch or continuous type of operation. A preferred type of operation is the continuous type. For example, the above described catalyst is disposed in a fixed bed in a reaction zone of a vertical tubular reactor and the alkylaromatic feed stock charged in an upflow or downflow manner, the reaction zone being maintained at a temperature of from about 200° to about 480° C., preferably at a temperature of from about 220° C. Although pressure does not appear to be an important variable with respect to the transalkylation reaction of this invention, the process is generally conducted in the presence of an imposed hydrogen pressure to provide from about 1 to about 10 moles of hydrogen per mole of hydrocarbon.

EXAMPLE 1

In this example, a catalytic composite of mordenite and alumina was prepared. Twenty pounds of commercial mordenite (100 H-Zeolon from Norton Chemical Company containing about 0.20 wt. % sodium as $Na_2O$ and 14 wt. % volatile matter as measured by weight loss on ignition at 900° C.) was thoroughly mixed with 24 pounds of a commercial boehmite alumina (Kaiser medium containing about 29 wt. % volatile matter). The said blend powder was admixed with approximately 19 pounds of 5.5 wt. % nitric acid solution by employing a continuous mixer. The resulting dough after intensive mixing was extruded through a 0.059 inch die. The extrudate was calcined in a belt calciner at conditions of 300° F. for 1 hour and 900° F. for 2 hours.

The extrudate was treated in a 15 wt. % ammonia solution via impregnation in a glass evaporator. After drying in the glass evaporator, the catalyst was oxidized in a belt calciner which maintains 300° F. for 1 hour and 900° F. for 2 hours. The finished catalyst was then coded TA-1.

EXAMPLE 2

In this example, TA-1 from Example 1 was calcined in a belt calciner which controls the temperature at 550° F. for 1 hour and 1100° F. for 2 hours. This finished catalyst was coded TA-1. The reason for this preparation is for comparison purposes because in the next example, TA-1 was boron impregnated and calcined.

EXAMPLE 3

In this example, a catalyst with a target level of 4 wt. % $B_2O_3$ on TA-1 is prepared. The following is a summary of preparation procedure.

(1) Weigh out 400 grams of TA-1 from Example 1 and place it in the glass evaporator.
(2) Add premixed solution into the glass evaporator. The solution is prepared by admixing 31.26 grams of $H_3BO_3$ in 550 ml of deionized water.
(3) Begin rotating the evaporator.
(4) Rotate the evaporator without steam for 1 hour.
(5) Turn the steam on and rotate evaporator with steam for 3 hours.
(6) Turn the steam off and continue rotating for 15 minutes.
(7) Unload the evaporator and proceed to the calcination.
(8) Calcine the catalyst in a belt calciner at condition of 600° F. in Zone I for 1 hour and 1200° F. in Zone II for 2 hours.
(9) Coded catalyst as TA-3.

EXAMPLE 4

Another catalyst composite consisting of an alumina matrix and Norton Zeolon 100-H mordenite was prepared as in Example 1 but Catapal alumina was used instead of Kaiser alumina. This extrudate was calcined for 1 hour at 300° F. and then 2 hours at 900° F. The extrudate was ammonia impregnated to a 15 wt. % $NH_3$ level and recalcined at 600° F. for 1 hour and 1200° F. for 2 hours, respectively in the belt calciner. This extruded catalyst was coded TA-4.

EXAMPLE 5

A catalyst composite consisting of a Catapal alumina matrix and Norton 100-H mordenite was prepared as in Example 1. This extrudate was calcined for 1 hour at 300° F. and 2 hours at 900° F. The extrudate was ammonia impregnated to a 15 wt. % $NH_3$ level and recalcined at 550° F. for 1 hour and 1100° F. for 2 hours, respectively in the belt calciner. This extrudate was coded TA-5.

EXAMPLE 6

100 gms. of the unammonia exchanged but calcined base from Example 4 was placed in the glass evaporator as in Example 3 and impregnated with a boric acid and ammonia solution. The solutions gave a finished target level of 15% $NH_3$ and 1.2 wt. % boria. This dried impregnated extrudate was calcined in the belt calciner at 550° F. for 1 hour and 1100° F. for 2 hours. This finished catalyst was coded TA-6.

EXAMPLE 7

Using the same alumina and mordenite zeolite blend made for Example 4, another extrudate was prepared. This time though the peptizing solution consisted not only of a 5.5 wt. % nitric acid but also 5 wt. % boric acid. The extrudate base was calcined at 300° F. for 1 hour and at 900° F. for 2 hours. Then the extrudate was ammonia impregnated as in Example 1. The final calcination step consisted of 1 hour at 550° F. and 2 hours at 1100° F. This catalyst was coded TA-7.

EXAMPLE 8

All six catalytic composites from Examples 1, 2, 3, 4, 5, 6 and 7 were evaluated in a transalkylation pilot plant. In this example 62.9 grams of catalyst (on a volatile free basis) was loaded in a reactor. Pure toluene, in an admixture with hydrogen to provide a hydrogen/hydrocarbon mole ratio of about 55, was charged downflow through a 100 cc bed at a weight hourly space velocity of 1.2. Transalkylation conditions consisted of an operating pressure of 400 psig and a temperature of the catalyst bed adjusted to effect a 40% conversion of the toluene feedstock. This temperature is an indication of the catalyst activity.

In toluene transalkylation another index which is used is the selectivity characterization of a catalyst and is defined as "mole % aromatic ring loss at 40 mole % conversion". The performance of the seven catalysts are presented in Table I.

TABLE I

| EXAMPLE | CATALYST PERFORMANCE SUMMARY | | | | | | |
|---|---|---|---|---|---|---|---|
|  | 1 | 2 | 3 | 4 | 5 | 6 | 7 |
| Catalyst Code | TA-1 | TA-2 | TA-3 | TA-4 | TA-5 | TA-6 | TA-7 |
| Temperature at 40% Conversion °F. (activity) | 716 | 690 | 759 | 712 | 691 | 706 | 691 |
| Mole % Ring Loss (selectivity) | 1.07 | 0.55 | 0.37 | 0.56 | 0.53 | 0.48 | 0.64 |

From these examples it is clear that the catalyst TA-3 with the boron addition improved significantly the mole % aromatic preservation at the same toluene conversion level. Other methods of boron addition (TA-7) showed no enhanced aromatic preservatin results.

The data presented in Table I demonstrates that a catalyst composite prepared according to the method of the present invention exhibits superior ability for the transalkylation of hydrocarbons with a low level of accompanying aromatic ring loss.

The foregoing specification an examples clearly illustrate the improvements encompassed by the present invention and the benefits to be afforded therefrom.

We claim as our invention:

1. A process for the transalkylation of alkylaromatic hydrocarbons at transalkylation conditions wherein said alkylaromatic hydrocarbons are contacted with a catalytic composite prepared by:
   (a) subjecting a mordenite alumina admixture to an aqueous ammoniacal treatment at a pH of at least about 9:5:
   (b) calcining the resulting mordenite alumina admixture from step (a);
   (c) subjecting the resulting calcined mordenite alumina admixto an aqueous solution containing a boron salt; and
   (d) calcining the resulting mordenite alumina admixture from step (c) to provide said catalytic composite.

2. The process of claim 1 wherein said transalkylation conditions include a temperature of from about 200° C. to about 480° C., a pressure from about atmospheric to about 1500 psig, and a hydrogen circulation rate to provide from about 1 to about 10 moles of hydrogen per mole of hydrocarbon.

3. The process of claim 1 wherein said alkylaromatic hydrocarbon is toluene.

* * * * *